US009801687B2

(12) United States Patent
Simpson et al.

(10) Patent No.: US 9,801,687 B2
(45) Date of Patent: Oct. 31, 2017

(54) PERFUSION SYSTEM WITH RFID

(71) Applicant: Sorin Group Italia S.r.l., Milan (IT)

(72) Inventors: Dennis Simpson, Superior, CO (US);
Derek E. Dahlinger, Arvada, CO (US);
Ivan Rossi, Poggio Rusco (IT)

(73) Assignee: Sorin Group Italia S.r.l., Milan (IT)

( * ) Notice: Subject to any disclaimer, the term of this patent is extended or adjusted under 35 U.S.C. 154(b) by 308 days.

(21) Appl. No.: 14/209,349

(22) Filed: Mar. 13, 2014

(65) Prior Publication Data
US 2014/0191026 A1 Jul. 10, 2014

Related U.S. Application Data

(62) Division of application No. 12/763,561, filed on Apr. 20, 2010, now Pat. No. 8,734,376.

(51) Int. Cl.
*A61M 1/36* (2006.01)
*A61B 19/00* (2006.01)
*A61B 90/90* (2016.01)

(52) U.S. Cl.
CPC .............. *A61B 19/44* (2013.01); *A61B 90/90* (2016.02); *A61M 1/3643* (2013.01);
(Continued)

(58) Field of Classification Search
CPC .............. A61M 1/3624; A61M 1/3643; A61M 1/3666; A61M 2205/3317;
(Continued)

(56) References Cited

U.S. PATENT DOCUMENTS 6,852,090 B2 2/2005 Burbank et al.
7,435,200 B2 10/2008 Kim et al.
(Continued)

FOREIGN PATENT DOCUMENTS

CN 101217988 A 7/2008
CN 101273361 A 9/2008
(Continued)

OTHER PUBLICATIONS

PALL Medical, "Blood Filtration Technology", 2005.*
(Continued)

*Primary Examiner* — Tatyana Zalukaeva
*Assistant Examiner* — Benjamin Klein
(74) *Attorney, Agent, or Firm* — Faegre Baker Daniels LLP

(57) ABSTRACT

The disclosure pertains to a perfusion system that is easy to set-up, use and monitor during a bypass procedure. In some embodiments, the disclosure pertains to a perfusion system in which at least some of the disposable components used with the perfusion system are configured to be able to communicate set-up and/or operational parameters to the perfusion system. In some embodiments, the disclosure pertains to a blood level sensor that can be used to monitor a blood level or volume within a blood reservoir. The blood level sensor may be utilized in an integrated perfusion system in which the disposable components are configured, as noted above, to communicate with the perfusion system. In some embodiments, the blood level sensor may be utilized with a perfusion system lacking communication with disposables.

12 Claims, 10 Drawing Sheets

(52) U.S. Cl.
CPC ......... *A61M 1/3666* (2013.01); *A61M 1/3624* (2013.01); *A61M 2205/3317* (2013.01); *A61M 2205/3375* (2013.01); *A61M 2205/3389* (2013.01); *A61M 2205/3569* (2013.01); *A61M 2205/3592* (2013.01); *A61M 2205/505* (2013.01)

(58) Field of Classification Search
CPC .. A61M 2205/3375; A61M 2205/3389; A61M 2205/3569; A61M 2205/3592; A61M 2205/505
See application file for complete search history.

(56) References Cited

U.S. PATENT DOCUMENTS

| | | | |
|---|---|---|---|
| 7,435,220 | B2 | 10/2008 | Ranucci |
| 7,639,136 | B1 * | 12/2009 | Wass ............... G06Q 10/08 340/572.1 |
| 7,762,989 | B2 | 7/2010 | Simpson |
| 7,927,286 | B2 | 4/2011 | Ranucci |
| 7,931,601 | B2 | 4/2011 | Ranucci |
| 7,955,295 | B2 | 6/2011 | Lee et al. |
| 8,105,265 | B2 | 1/2012 | Demers et al. |
| 8,888,730 | B2 | 11/2014 | Rossi et al. |
| 9,132,214 | B2 | 9/2015 | Rossi et al. |
| 2002/0103453 | A1 | 8/2002 | Burbank et al. |
| 2004/0051368 | A1 * | 3/2004 | Caputo ............... A61M 5/142 299/1.9 |
| 2005/0277890 | A1 * | 12/2005 | Stewart ............... A61M 5/172 604/189 |
| 2006/0044137 | A1 | 3/2006 | Morris et al. |
| 2008/0210606 | A1 * | 9/2008 | Burbank ............... C02F 1/444 210/85 |
| 2009/0012449 | A1 | 1/2009 | Lee et al. |
| 2009/0088731 | A1 | 4/2009 | Campbell et al. |
| 2009/0099498 | A1 * | 4/2009 | Demers ............... A61M 1/106 604/6.09 |
| 2009/0204075 | A1 | 8/2009 | Simpson |
| 2010/0022988 | A1 * | 1/2010 | Wochner ........... A61M 5/14244 604/506 |
| 2011/0181394 | A1 | 7/2011 | Blair |
| 2011/0230822 | A1 | 9/2011 | Lee et al. |
| 2011/0257576 | A1 | 10/2011 | Simpson et al. |
| 2014/0079590 | A1 | 3/2014 | Rossi et al. |
| 2015/0105642 | A1 | 4/2015 | Rossi et al. |

FOREIGN PATENT DOCUMENTS

| | | |
|---|---|---|
| CN | 101669122 A | 3/2010 |
| CN | 104640582 A | 5/2015 |
| JP | H04111353 U | 9/1992 |
| JP | H11319075 A | 11/1999 |
| JP | 2004187942 A | 7/2004 |
| JP | 2004249110 A | 9/2004 |
| JP | 2006034845 A | 2/2006 |
| JP | 2008517651 A | 5/2008 |
| JP | 2009064282 A | 3/2009 |
| JP | 2009157413 A | 7/2009 |
| JP | 2013524921 A | 6/2013 |
| JP | 2015529126 A | 10/2015 |
| WO | WO02095675 A1 | 11/2002 |
| WO | WO03026724 A1 | 4/2003 |
| WO | 2006047147 A1 | 5/2006 |
| WO | WO2006083933 A1 | 8/2006 |
| WO | WO2007120812 A2 | 10/2007 |
| WO | 2011132123 A1 | 10/2011 |
| WO | WO2011144747 A1 | 11/2011 |

OTHER PUBLICATIONS

European Search Report issued in EP Application No. 10160466, dated Aug. 30, 2010, 3 pages.
European Search Report issued in EP Application No. 12187203, mailed Nov. 1, 2013, 7 pages.
European Search Report issued in EP Application No. 12194981, dated Feb. 4, 2013, dated Feb. 13, 2013.
International Search Report and Written Opinion issued in PCT/IB2011/051643, dated Jul. 11, 2011, 9 pages.
International Search Report and Written Opinion issued in PCT/IB2013/056071, dated Nov. 1, 2013, dated Nov. 8, 2013, 10 pages.

* cited by examiner

PERFUSION SYSTEM WITH RFID

CROSS-REFERENCE TO RELATED APPLICATION

This application is a division of U.S. application Ser. No. 12/763,561, filed Apr. 20, 2010, which is herein incorporated by reference in its entirety.

TECHNICAL FIELD

The disclosure pertains generally to perfusion systems and more particularly to integrated perfusion systems configured to communicate component-specific information between system components.

BACKGROUND

Perfusion entails encouraging physiological solutions such as blood through the vessels of the body or a portion of a body of a human or animal. Illustrative examples of situations that may employ perfusion include extracorporeal circulation during cardiopulmonary bypass surgery as well as other surgeries. In some instances, perfusion may be useful in providing extracorporeal circulation during various therapeutic treatments. Perfusion may be useful in maintaining the viability of body parts such as specific organs or limbs, either while the particular body part remains within the body, or while the body part is exterior to the body such as for transplantation or if the body part has been temporarily removed to provide access to other body structures. In some instances, perfusion may be used for a short period of time, typically defined as less than about six hours. In some cases, perfusion may be useful for extended periods of time that are greater than about six hours.

In some instances, blood perfusion systems include one or more pumps in an extracorporeal circuit that is interconnected with the vascular system of a patient. Cardiopulmonary bypass (CPB) surgery typically requires a perfusion system that allows for the temporary cessation of the heart by replacing the function of the heart and lungs. This creates a still operating field and allows for the surgical correction of vascular stenosis, valvular disorders, and congenital heart and great vessel defects. In perfusion systems used for cardiopulmonary bypass surgery, an extracorporeal blood circuit is established that includes at least one pump and an oxygenation device to replace the functions of the heart and lungs.

More specifically, in cardiopulmonary bypass procedures, oxygen-poor blood (i.e., venous blood) is gravity-drained or vacuum suctioned from a large vein entering the heart or other veins (e.g., femoral) in the body and is transferred through a venous line in the extracorporeal circuit. The venous blood is pumped to an oxygenator that provides for oxygen transfer to the blood. Oxygen may be introduced into the blood by transfer across a membrane or, less frequently, by bubbling oxygen through the blood. Concurrently, carbon dioxide is removed across the membrane. The oxygenated blood is then returned through an arterial line to the aorta, femoral, or other main artery.

A perfusion system typically includes various fluid circuitry and components that are configured by medical personnel prior to the bypass procedure. This can be a time consuming process and may require significant manual input of information relating to various components of the system.

SUMMARY

According to an embodiment of the present invention, an integrated perfusion system includes a heart lung machine and one or more disposable elements that are configured to be used in conjunction with the heart lung machine. The heart lung machine includes a plurality of pump modules, each of which has a control unit. The heart lung machine also includes a controller that is in communication with each of the pump module control units, an input device that is in communication with the controller and that is configured to accept operational settings information from a user and an output device that is in communication with the controller and that is configured to display operational parameters of the plurality of pump modules. The heart lung machine also includes an RF sensor that is in communication with the controller. The one or more disposable elements include an RFID tag that is programmed with disposable element-specific information that can be read by the RF sensor and used by the controller to regulate operation of the heart lung machine in place of at least some operational parameters otherwise inputted by the user.

According to another embodiment of the present invention, a method of configuring an integrated perfusion system having a heart lung machine with an RF sensor and a disposable component with an RFID tag includes attaching the disposable component having an RFID tag to the heart lung machine. The RFID tag is read with the RF sensor, and operation of the heart lung machine is configured based at least in part upon information provided from the RFID tag to the RF sensor.

According to another embodiment of the present invention, a heart lung machine pack includes a housing configured to hold a plurality of disposable elements for a heart lung machine, a tubing set and a component. The tubing set includes a first RFID tag secured to the tubing set and is configured for one-time use with a heart lung machine. The component has a second RFID tag secured to the component and is configured for one-time use with a heart lung machine.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

The disclosure pertains to a perfusion system that is easy to set-up, use and monitor during a bypass procedure. In some embodiments, the disclosure pertains to a perfusion system in which at least some of the disposable components used with the perfusion system are encoded with set-up and/or operational parameters. In some embodiments, the disclosure pertains to a blood level sensor that can be used to monitor a blood level or volume within a blood reservoir. The blood level sensor may be utilized in an integrated perfusion system in which the disposable components are configured, as noted above, to communicate with the perfusion system. In some embodiments, the blood level sensor may be utilized with a perfusion system lacking communication with disposables.

Figure 1:
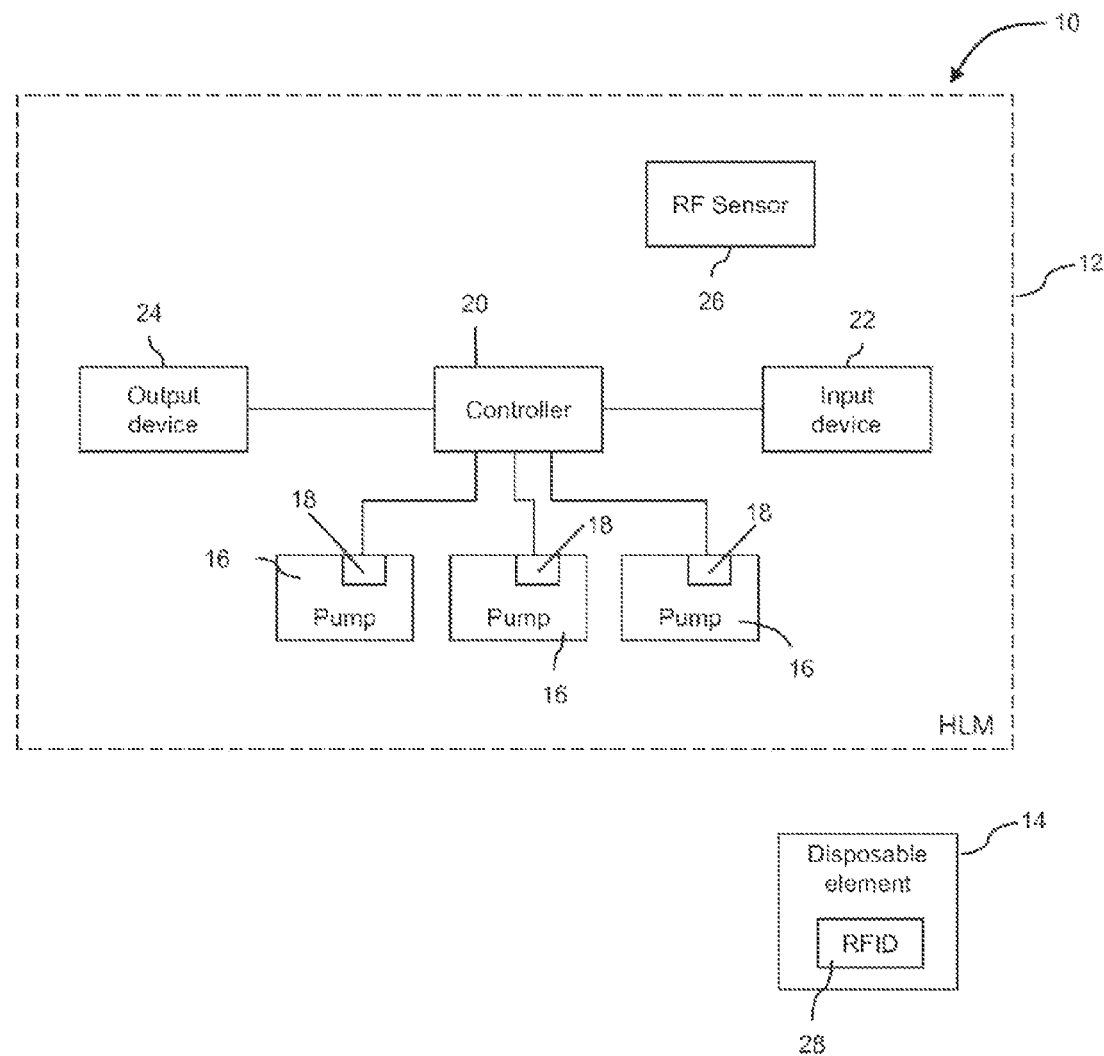
FIG. 1 is a schematic illustration of an integrated perfusion system in accordance with an embodiment of the invention.

FIG. 1 is a schematic illustration of an integrated perfusion system 10 including a heart lung machine (HLM) 12 and a disposable element 14. While only a single disposable element 14 is shown for ease of illustration, in many embodiments a plurality of different disposable elements 14 may be utilized in combination with the HLM 12. Each of the HLM 12 and the disposable element 14 will be described in greater detail subsequently. The HLM 12 includes a number of different components. It is to be understood that the particular components illustrated herein as being part of the HLM 12 is merely an example, as the HLM 12 may include other components or different numbers of components.

In the illustrated embodiment, the HLM 12 includes three pump modules 16, but may include as few as two pump modules 16 or as many as six or seven pump modules 16. In some embodiments, the pump modules 16 may be roller or peristaltic pumps. In some embodiments, one or more of the pump modules 16 may be centrifugal pumps. Each of the pump modules 16 may be used to provide fluid or gas for delivery to or removal from the heart chambers and/or surgical field. In an illustrative but non-limiting example, one pump module 16 draws blood from the heart, another provides surgical suction and a third provides cardioplegia fluid (high potassium solution to arrest the heart). Additional pump modules 16 (not shown) may be added to provide additional fluid transfer.

Each pump module 16 includes a control unit 18. In some embodiments, each control unit 18 may be configured to operate and monitor the operation of the particular pump module 16 to which it is attached or otherwise connected to. In some embodiments, each control unit 18 may include one or more input devices (not illustrated) such as switches, knobs, buttons, touch screens and the like so that the perfusionist may adjust the operation of the particular pump module 16. Each pump module 16 may include an alpha-numeric display that the control unit 18 can use to display, for example, the value of a setting, the value of a current operating parameter, confirmation that the pump module 16 is operating normally, and the like.

The HLM 12 includes a controller 20 that is in communication with the control units 18 and that is configured to operate the HLM 12. In some embodiments, the controller 20 is configured to monitor one or more sensors that may be distributed on the HLM 12 and/or within the disposable element 14 to monitor operation of the HLM 12. Examples of such sensors (not illustrated for ease of illustration) include but are not limited to flow meters, pressure sensors, temperature sensors, blood gas analyzers and the like.

While the control units 18 and the controller 20 are illustrated as distinct elements, in some embodiments it is contemplated that these elements may be combined in a single controller. In some embodiments, it is contemplated that the control units 18, in combination, may be configured to operate the HLM 12, thereby negating a need for the controller 20.

The controller 20 communicates with an input device 22 and an output device 24. The input device 22 may be used by the perfusionist to enter information that is not otherwise entered into the control units 18. The output device 24 may be used by the HLM 12 to display pertinent information to the perfusionist. In some embodiments, the input device 22 may be a key pad, a keyboard, a touch screen, and the like. In some embodiments, the output device 24 may be a monitor. In some embodiments, either of the input device 22 and/or the output device 24 may be a computer such as a personal computer, a laptop computer, a notebook computer or a tablet computer. In some cases, the input device 22 and the output device 24 may be manifested in a single computer.

The HLM 12 also includes an RF sensor 26. In some embodiments, the RF sensor 26 may be configured to receive information from an active RFID tag placed on the disposable element 14. In some embodiments, the RF sensor 26 may be a hand held device that is used to scan a passive RFID tag on the disposable element 14. According to other embodiments, the RF sensor 26 is replaced with any of a variety of known wireless communication receivers. The disposable element 14 includes an RFID tag 28. According to various embodiments, the disposable element 14 includes either an active RFID tag or a passive RFID tag (or both) configured to communicate with the RF sensor 26. In other embodiments, the RFID tag 28 is replaced with any of a variety of known wireless communication transmitters.

Passive RFID tags lack a power supply, and instead are powered by an induced current caused by an incoming radio-frequency scan. Because there is no onboard power supply, a passive RFID tag is smaller and less expensive. An active RFID tag includes an onboard power supply such as a battery. While this increases the size and expense of the RFID tag, an advantage is that the RFID tag can store more information and can transmit further. RFID tags, whether active or passive, may be selected to transmit at a variety of frequencies depending on need. Options include low frequency (about 100 to 500 kilohertz), high frequency (about 10 to 15 megahertz), ultra high frequency (about 860 to 960 megahertz) and microwave (about 2.45 gigahertz).

As noted above, the disposable element 14 may be considered as generically representing one, two or a plurality of different disposable elements that may be used in conjunction with the HLM 12. Illustrative but non-limiting examples of disposable elements 14 include tubing sets, blood reservoirs, oxygenators, heat exchangers and arterial filters. In some embodiments, a tubing set includes a number of different tubes, potentially of different lengths and sizes, for providing fluid flow between components of the HLM 12 as well as providing fluid flow between the HLM 12 and a patient.

In some embodiments, the disposable element 14 may be a blood reservoir such as a venous blood reservoir, a vent blood reservoir, a cardiotomy or suction blood reservoir. In some embodiments, the disposable element 14 may be a blood reservoir that combines one or more of a venous blood reservoir, a vent reservoir and/or a suction reservoir in a single structure. In some embodiments, one or more of the aforementioned sensors may be disposable elements that include an RFID tag 28 either to provide information identifying the sensor or even for transmitting sensed values to the controller 20.

The RFID tag 28 may be attached to the disposable element 14 in any appropriate manner. In some embodiments, the RFID tag 28 may be adhesively secured to the disposable element 14. In some embodiments, the RFID tag 28 may be molded into the disposable element 14. In some embodiments, the RFID tag 28 may be a stand alone card, similar in size and shape to a credit card, that may simply be packed with the disposable element 14 in such a way that it can be removed by the user and swiped by the RF sensor 26. However the RFID tag 28 is attached, the RFID tag 28 may be programmed with or otherwise configured to include a wide variety of information pertaining to the disposable element 14.

In some embodiments, the RFID tag 28 may include data or identifying information for the disposable element 14. Illustrative but non-limiting examples of identifying information include the name of the particular disposable element 14, a reference code, a serial number, a lot number, an expiration date and the like. In some embodiments, this information may be communicated to the controller 20 and may, for example, be used by the controller 20 to confirm that the proper disposable elements 14 are being used for a particular setting, patient or the like. As an example, the controller 20 may recognize that a pediatric tubing set is being used in combination with an adult-sized blood reservoir or other component. As another example, the controller 20 may recognize that an expected component is missing. There are a variety of other potential mismatches in equipment that may be recognized by the controller 20 as a result of the information provided by the RFID tag 28 attached to each of the one or more disposable elements 14.

In some embodiments, the RFID tag 28 may include descriptive or design information for the disposable element 14. Illustrative but non-limiting examples of descriptive or design information include specific materials, a list of components, priming volume of a component or tubing circuit, tubing size, tubing length, minimum and maximum working pressures, minimum and maximum working volume, and the like. In some embodiments, this information may be communicated to the controller 20 and may be used by the controller 20 to at least partially configure and/or operate the HLM 12. As an example, the controller 20 may use the sizing information provided from each of the disposable elements 14 to determine a working blood volume for the HLM 12.

In some embodiments, the information obtained from the RFID tag 28 may also be provided to the perfusionist. In some embodiments, the output device 24 may be configured to provide alphanumeric or graphical representations of the obtained information. In some cases, the RFID tag 28 may include instructional information that may be displayed by the output device 24 in order to instruct the perfusionist in optimal setup and/or operation of a particular disposable element 14. In various embodiments, the output device 24 may be a computer such as a personal computer, a laptop computer, a notebook computer or a tablet computer. In some embodiments, the RFID tag 28 may include displayable information that, for example, suggests an optimal circuit design based upon the specific components being used, or perhaps updated use instructions. In some embodiments, information from the RFID tag 28 is displayed on an integrated data management system (DMS).

In some embodiments, the RFID tag 28 may include information that a manufacturer of the disposable element 14 wants to provide to the user. Examples of such information may include technical features of the disposable element 14 that have changed from a previous version or even a previous batch. Another example includes information that can be displayed by the output device 24 that require the user to acknowledge receipt of the information before the controller 20 proceeds with a particular procedure. In some cases, the RFID tag 28 may receive error messages from the controller 20, and the RFID tag 28 may then be returned to the manufacturer, thereby providing the manufacturer with feedback regarding the performance of the disposable element 14 as well as other components.

Figure 2:
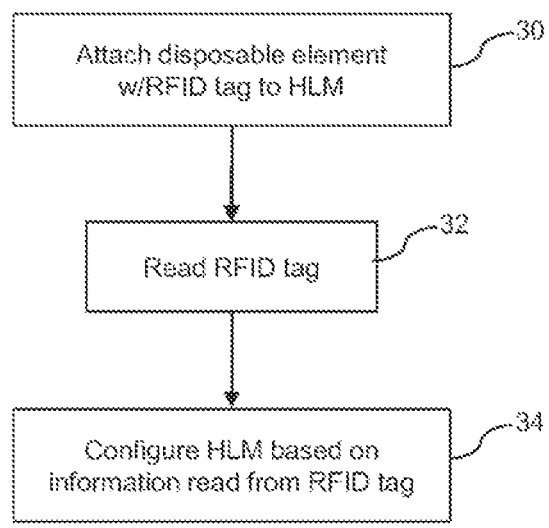
FIG. 2 is a flow diagram illustrating a method that can be carried out by the integrated perfusion system of FIG. 1.

FIG. 2 is a flow diagram illustrating a method that may be carried out using the perfusion system 10 of FIG. 1. A disposable element 14 having an RFID tag 28 may be attached to the HLM 12, as generally shown at block 30. At block 32, the RFID tag 28 is read. As noted above, the RFID tag 28 may be an active RFID tag or a passive RFID tag. In some embodiments, the RFID tag 28 may be read before the disposable element 14 is attached to the HLM 12. In some embodiments, the RFID tag 28 may be read after attachment. At block 34, the HLM 12 is configured based at least in part upon information that was read from the RFID tag 28 at block 32. In some embodiments, the controller 20 automatically configures the HLM 12 in response to this information.

Figure 3:
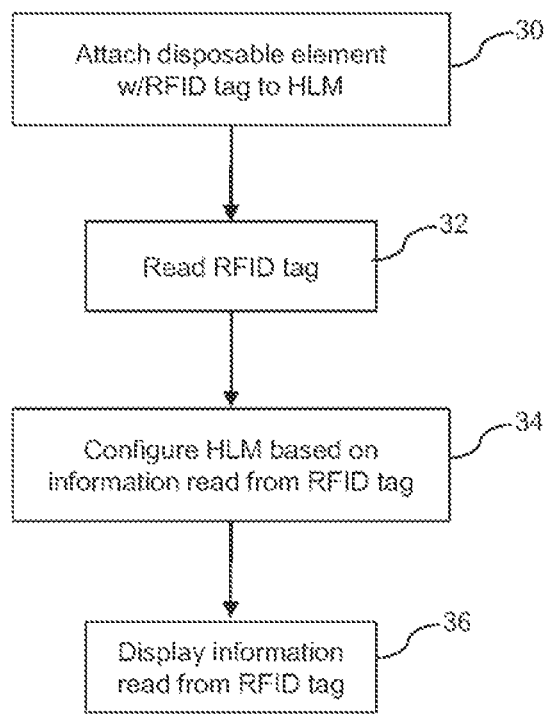
FIG. 3 is a flow diagram illustrating a method that can be carried out by the integrated perfusion system of FIG. 1.

FIG. 3 is a flow diagram illustrating a method that may be carried out using the perfusion system 10 of FIG. 1. A disposable element 14 having an RFID tag 28 may be attached to the HLM 12, as generally shown at block 30. At block 32, the RFID tag 28 is read. The RFID tag 28 may be read either before or after the disposable element 14 is attached to the HLM 12. At block 34, the HLM 12 is configured based at least in part upon information that was read from the RFID tag 28 at block 32. In some embodiments, the controller 20 automatically configures the HLM 12 in response to this information. At least some of the information read from the RFID tag 28 may be displayed on the output device 24, as seen at block 36.

Figure 4:
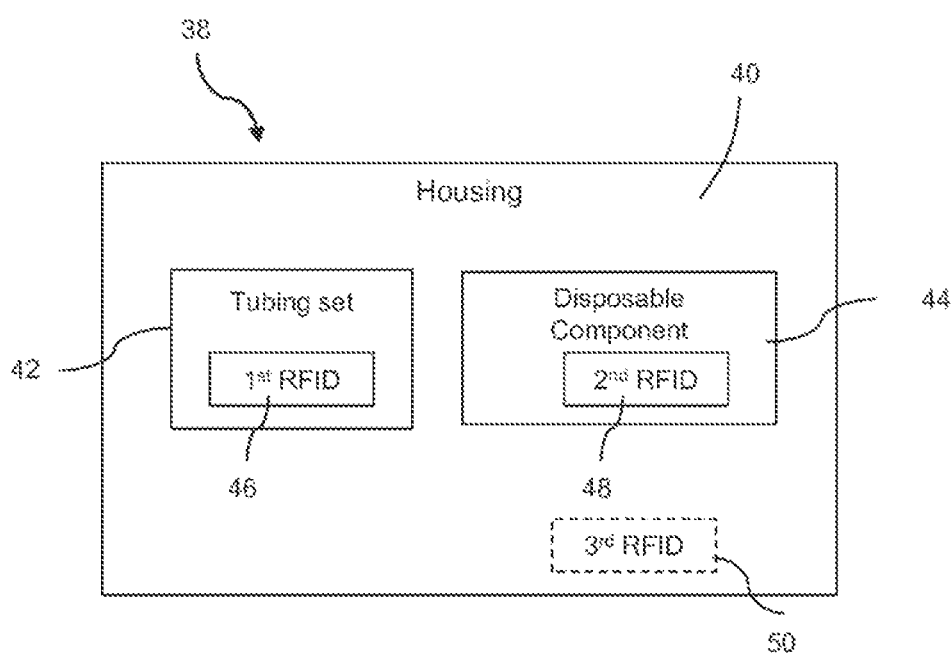
FIG. 4 is a schematic illustration of a heart lung machine pack that may be utilized with the integrated perfusion system of FIG. 1.

FIG. 4 is a schematic illustration of a heart lung machine pack 38 that may be utilized with the perfusion system 10 of FIG. 1. In some embodiments, the heart lung machine pack 38 may include all of the disposable elements 14 that will be used together for a particular patient and may be customized for the particular patient. In some embodiments, the heart lung machine pack 38 may include a housing 40 that, once filled, can be sealed up to keep the contents clean and sterile In the illustrated embodiment, the heart lung machine pack 38 includes a tubing set 42 and a disposable component 44. The tubing set 42 may include a plurality of different tubes. The disposable component 44 may be any of the disposable components discussed above with respect to the disposable element 14. In some embodiments, the heart lung machine pack 38 will include a plurality of different disposable components 44. The tubing set 42 includes a first RFID tag 46 while the disposable component 44 includes a second RFID tag 48. As discussed above, each of the first RFID tag 46 and the second RFID tag 48 may be either active or passive RFID tags and may include readable information pertaining to the component to which they are attached. In some instances, the housing 40 may include a third RFID tag 50 that, for example, identifies the contents of the heart lung machine pack 38. In some embodiments, the first RFID tag 46 and the second RFID tag 48 may not be included, as the third RFID tag 50 may be encoded with all of the information for the tubing set 42 and the disposable component 44.

Figure 5:
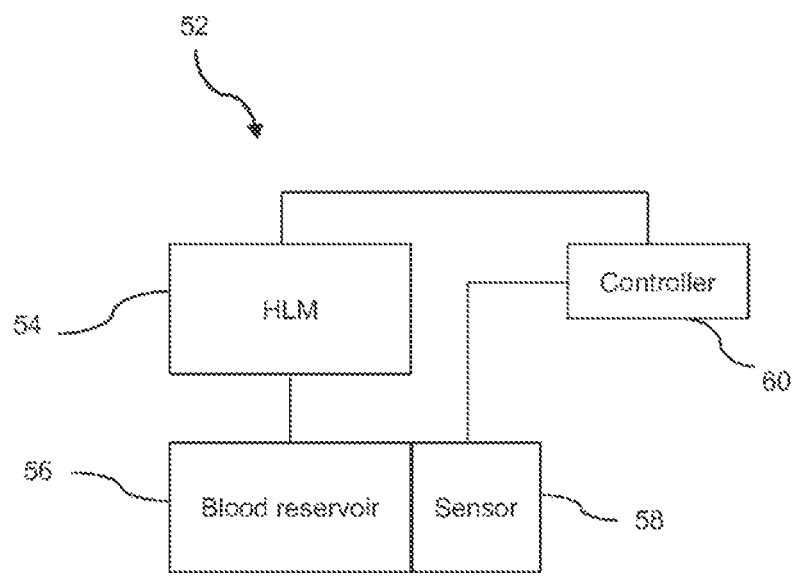
FIG. 5 is a schematic illustration of a perfusion system in accordance with an embodiment of the invention.

FIG. 5 is a schematic illustration of a perfusion system 52. The perfusion system 52 includes an HLM 54 that in some embodiments may be similar in structure and operation to the HLM 12 discussed with respect to FIG. 1. The perfusion system 52 also includes a blood reservoir 56, a blood level sensor 58 and a controller 60. The blood reservoir 56 may be a venous blood reservoir, a vent blood reservoir, a cardiotomy or suction blood reservoir. In some embodiments, the blood reservoir 56 may be a blood reservoir that combines one or more of a venous blood reservoir, a vent reservoir and/or a suction reservoir in a single structure.

The blood level sensor 58 may be configured to continuously monitor a variable blood level within the blood reservoir 56. The blood level sensor may be chosen from a variety of different sensing technologies. In some embodiments, as will be discussed subsequently with respect to FIGS. 12 and 13, the blood level sensor 58 may be an ultrasonic sensor in which ultrasound is used to detect the blood level within the blood reservoir 56. In some embodiments, the blood level sensor 58 may be an optical sensor in which a laser beam or light from an infrared light source is reflected by the liquid-air interface and the reflected light beam is detected by the blood level sensor 58. According to exemplary embodiments, the blood level sensor 58 is an optical distance sensor of the type commercially sold by Leuze electronic GmbH located in Owen/Teck, Germany (e.g., ODSL8, ODSL 30, or ODS 96). In some embodiments, the blood level sensor 58 may be a load cell or scale that is configured to measure a mass of the blood reservoir 56 and thereby determine the volume of blood therein.

In some embodiments, the blood level sensor 58 may be a capacitive sensor (better illustrated in subsequent Figures) that outputs an electrical signal that is proportional to or otherwise related to a blood level within the blood reservoir 56. The electrical signal may be communicated in either a wired or wireless fashion to the controller 60. While the controller 60 is shown as a distinct element, in some embodiments the controller 60 is manifested as part of a controller (similar to the controller 20) operating the HLM 54.

In some embodiments, the blood level sensor 58 may be modeled after capacitive sensors (e.g., CLC or CLW series) available commercially from Sensortechnics GmbH located in Puchheim, Germany, which are configured to provide contact-free measurement of continuous liquid level. The sensor available from Sensortechnics may be disposed on an outer surface of a container and provides an electrical signal representative of the liquid level within the container. In some instances, the Sensortechnics sensor may be spaced as much as about five millimeters from the liquid within the sensor, with no more than about twenty percent air gap between the sensor and the liquid. According to various embodiments, the capacitive sensor 58 is molded inside the blood reservoir 56, such that only the connector is accessible outside the reservoir. In these embodiments, the sensor 58 is protected by the plastic material of the blood reservoir.

In some embodiments, the sensor may undergo an initial configuration to adapt the sensor to the particulars of the container itself as well as the liquid within the container. In some embodiments, the blood level sensor 58 has a five pin electrical connection, including a voltage source, an analog signal out, a digital signal out, a teach-in pin and a ground. In some embodiments, the level sensor 58 is a capacitive sensor such as the Balluff SmartLevel sensor commercially sold by Balluff GmbH located in Neuhausen, Germany.

The controller 60 may receive an electrical signal that is proportional to or at least related to a blood level within the blood reservoir 56. The controller 60 may calculate a blood volume based on this electrical signal as well as a known shape or geometry of the blood reservoir 56. In some embodiments, the blood reservoir 56 may include an RFID tag (not illustrated) that provides the controller 60 with information pertaining to the known geometry of the blood reservoir 56.

If the blood reservoir 56 is a hard shell blood reservoir, the known geometry of the blood reservoir 56 may include the cross-sectional area of the blood reservoir 56, or a width and depth of the blood reservoir 56 as well as details on how this cross-sectional area varies relative to height within the blood reservoir 56. If the blood reservoir 56 is a soft shell reservoir, the known geometry may be based at least in part upon a known lateral expansion rate of the soft shell reservoir relative to the blood level within the blood reservoir 56.

Figure 6:
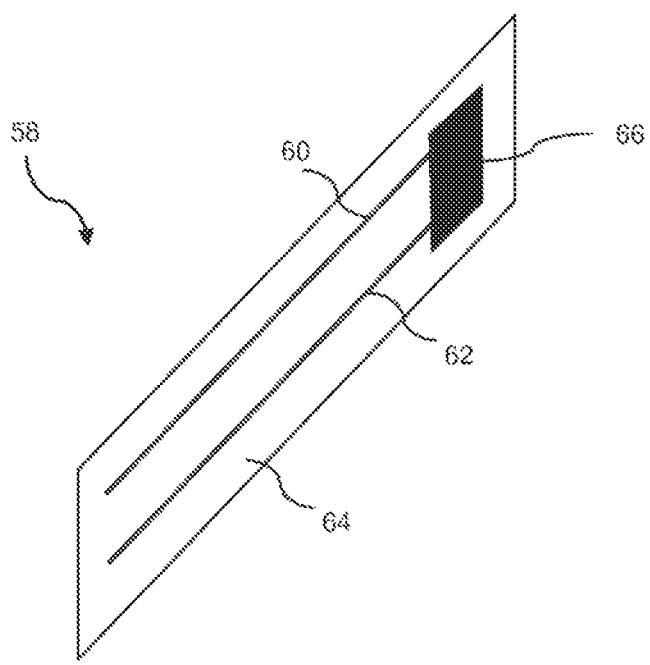
FIG. 6 is an illustration of a blood level sensor that may be utilized with the perfusion system of FIG. 5.

As can be seen in FIG. 6, the blood level sensor 58 includes a first elongate electrode 60 and a second elongate electrode 62. The first elongate electrode 60 and the second elongate electrode 62 are disposed along a flexible substrate 64. In some embodiments, the flexible substrate 64 may include an adhesive layer that can be used to secure the blood level sensor 58 to the blood reservoir 56. A connector socket 66 is secured to the flexible substrate 64 and is electrically connected to the first elongate electrode 60 and the second elongate electrode 62 in order to permit an electrical connection between the first and second electrodes 60, 62 and an electrical cable (not illustrated in this Figure). In some embodiments, rather than an elongate sensor, the blood level sensor 58 may include two or more distinct SMARTLEVEL™ capacitive sensors such as those available commercially from Balluff. These sensors may provide a binary, yes/no signal. By locating several of these sensors at differing levels proximate the blood reservoir 56, the blood level within the blood reservoir 56 may be determined.

Figure 7:
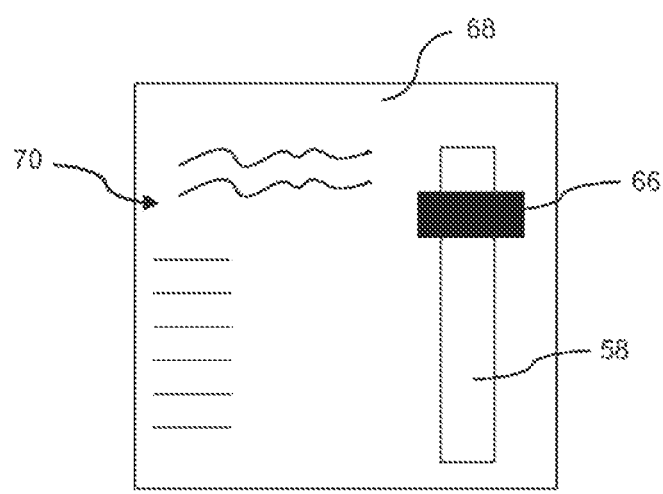
FIG. 7 is an illustration of a blood level sensor incorporated into a label that may be utilized with the perfusion system of FIG. 5.

In some embodiments, the blood level sensor 58 may be attached to or otherwise integrated into a label 68 as seen in FIG. 7. The label 68 may include various indicia 70 such as use instructions, volume indicators and the like. In some embodiments, the label 68 may include an adhesive side for attachment to an outer surface of the blood reservoir 56. In some embodiments, the label 68 is oriented on the blood reservoir such that a lower portion of the blood level sensor 58 is aligned at or near a bottom of the blood reservoir 56.

Figure 12:
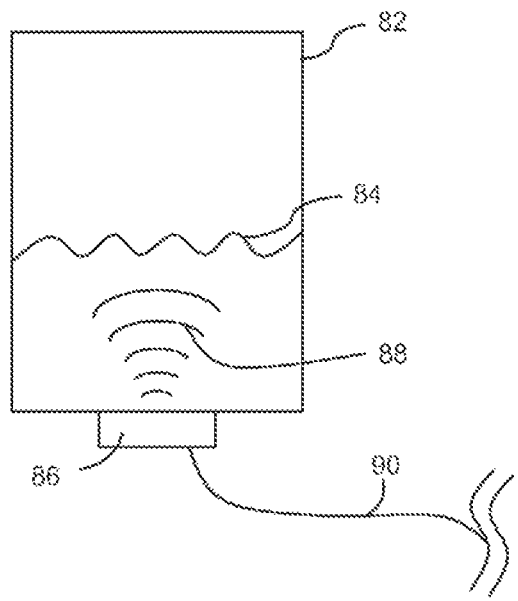
FIG. 12 is an illustration of a blood reservoir including a blood level sensor in accordance with an embodiment of the invention.
Figure 13:
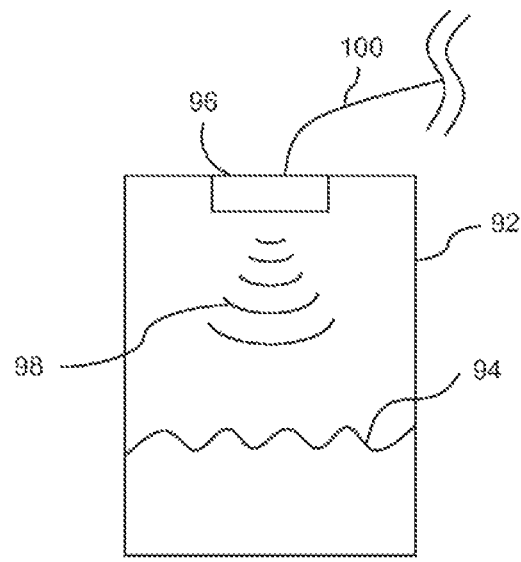
FIG. 13 is an illustration of a blood reservoir including a blood level sensor in accordance with an embodiment of the invention.

In some embodiments, the blood level sensor may be an ultrasonic blood level sensor, as illustrated in FIGS. 12 and 13. FIG. 12 is an illustration of a blood reservoir 82 that contains a volume of blood. The volume of blood defines an interface 84 between the volume of blood and the air or other fluid within the blood reservoir 82. In some embodiments, an ultrasonic transducer 86 that is located at or near a lower surface of the blood reservoir 82 can be used to locate the interface 84 by transmitting ultrasonic waves 88 towards the interface 84. The reflectance of the ultrasonic waves 88 depend at least in part upon the fluid they are passing through. Thus, by measuring the reflectance, the ultrasonic transducer 86 can determine how far away the interface 84 is and thereby determine the fluid level. Based on the fluid level and the geometric configuration of the blood reservoir 82, a controller may determine the blood volume within the blood reservoir 82. In some embodiments, a cable 90 transmits a signal from the ultrasonic transducer 86 to the controller. In some embodiments, the information is transmitted wirelessly, such as via an RFID tag attached to the ultrasonic transducer.

FIG. 13 is similar to FIG. 12, but shows a blood reservoir 92 having a blood volume defining an interface 94. In this embodiment, an ultrasonic transducer 96 is located at or near a top of the blood reservoir 92 and transmits ultrasonic waves 98 downward towards the interface 94. In some embodiments, a cable 100 transmits a signal from the ultrasonic transducer 96 while in other embodiments this is done wirelessly, such as with an RFID tag attached to the ultrasonic transducer 96. A primary difference between the embodiments shown in FIGS. 12 and 13 is that in FIG. 12, the interface 84 is detected from below, or through the blood, while in FIG. 13 the interface 94 is detected from above.

In some embodiments, the blood level sensor may be an infrared (IR) light blood level sensor. In some embodiments, an infrared light source positioned at or near a lower surface of the blood reservoir 82 may be used to locate a fluid/air interface within the blood reservoir 82 by transmitting infrared light towards the interface. Alternatively, the infrared light blood level sensor may be located above the interface. In some embodiments, the infrared light blood level sensor may be located a short distance away from the blood reservoir 82 and thus can be attached to a mechanical holder for the blood level reservoir 82.

In some instances, the infrared light is reflected back towards the infrared light blood level sensor. By measuring the reflectance, the location of the interface may be determined. In some embodiments, the infrared light travels through the blood to an infrared light sensor located opposite the infrared light blood level sensor. By detecting changes in the received light, the interface location may be determined. By combining the interface location with known geometric parameters of the blood reservoir 82, the controller 20 can determine the blood volume within the blood reservoir 82. In some embodiments, this information is transmitted wirelessly to the controller 20, such as via an RFID tag attached to the infrared light blood level sensor.

Figure 8:
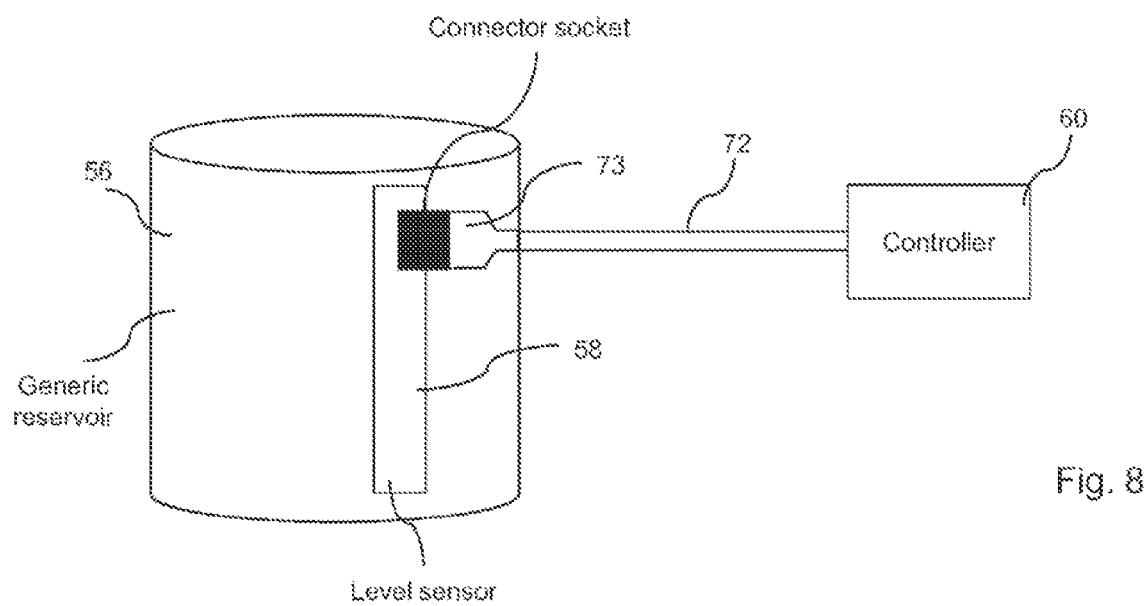
FIG. 8 is an illustration of a blood reservoir including a blood level sensor in accordance with an embodiment of the invention.

FIG. 8 is an illustration of the blood level sensor 58 attached to the blood reservoir 56. An electrical cable 72 provides an electrical connection between the blood level sensor 58 and the controller 60. The electrical cable 72 includes a plug 73 that is configured to connect to the electrical connector 66. In some embodiments, the plug 73 includes circuitry that converts a detected capacitance into a voltage signal that the controller 60 can use to calculate the blood volume. In some embodiments, the plug 73 further includes circuitry to calculate the blood volume.

Figure 9:
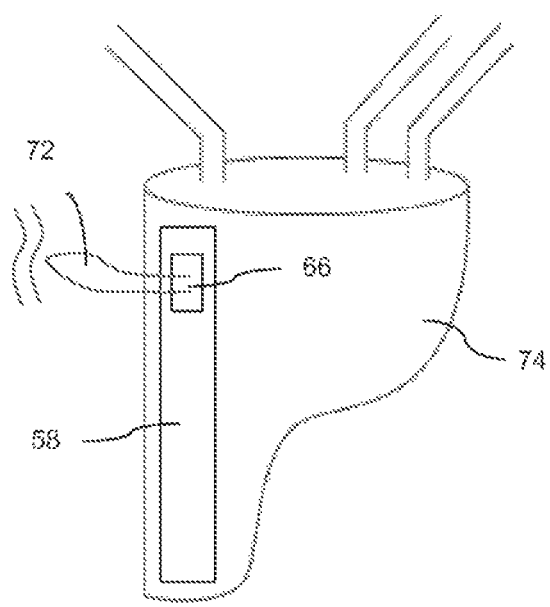
FIG. 9 is an illustration of a hard shell blood reservoir including a blood level sensor in accordance with an embodiment of the invention.
Figure 10:
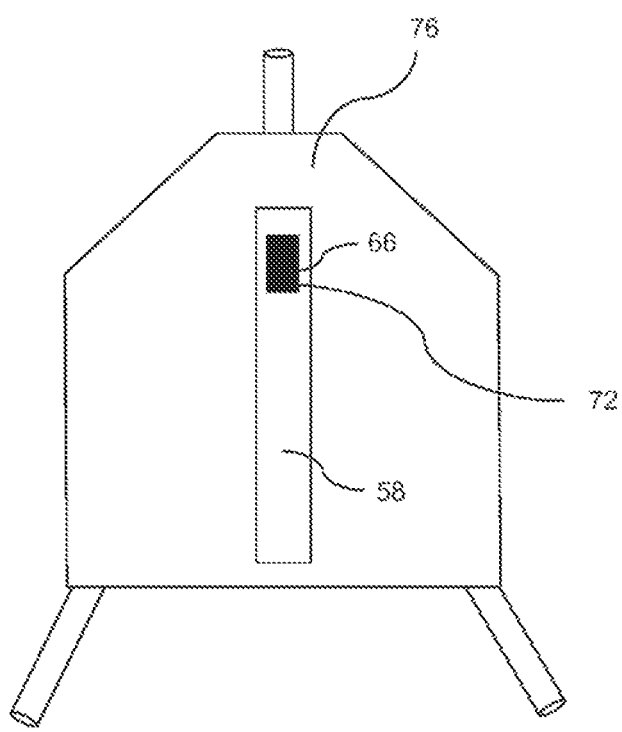
FIG. 10 is an illustration of a soft shell blood reservoir including a blood level sensor in accordance with an embodiment of the invention.

As noted above, the blood reservoir 56 may be either a hard shell reservoir or a soft shell reservoir. FIG. 9 illustrates a hard shell reservoir 74 bearing the blood level sensor 58 while FIG. 10 illustrates a soft shell reservoir 76 including the blood level sensor 58. In either case, the reservoir may be constructed to include the blood level sensor 58. In some embodiments, the blood level sensor 58 may be adhesively secured to an existing blood reservoir.

Figure 11:
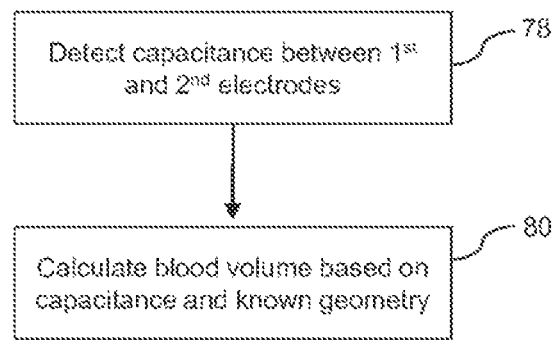
FIG. 11 is a flow diagram illustrating a method that can be carried out using the perfusion system of FIG. 5.

FIG. 11 is a flow diagram illustrating a method that may be carried out using the perfusion system 52 of FIG. 5. A capacitance between first and second electrodes may be detected, as referenced at block 78. In some embodiments, as discussed above, the capacitance may be converted into an electrical signal representing the blood level by circuitry within the plug 73. In embodiments using the CLC series Sensortechnics sensor, for example, the sensor will output a voltage between 0.5 and 4.5 volts. Assuming the sensor pad is appropriately located on the reservoir, this voltage indicates a level or height of the liquid in the reservoir. At block 80, the controller 60 may calculate a blood volume that is based upon the detected capacitance and a known dimensions or geometry of the blood reservoir 56. In some embodiments, the controller 60 (or other circuitry within the HLM 54) may provide the circuitry in the plug 73 with sufficient information (e.g., dimensions or geometry) regarding the blood reservoir 56 to permit the circuitry to perform the blood volume calculation. In some embodiments, the calculated blood volume is communicated to the HLM 54 so that it may adjust an operating parameter of the HLM 54. In various exemplary embodiments, the HLM 54 may alter a pump speed to either increase or decrease blood flow into or out of the blood reservoir 56. It may be important, for example, to prevent the blood level in the reservoir 56 from moving below a certain minimum level or volume. Accordingly, in various embodiments, the HLM will compare the blood level or volume to this minimum level and adjust pump speed appropriately.

According to other embodiments, the HLM may use the blood volume information for a variety of applications, including for example auto-regulation of pump occlusion, auto-loading of pump segments, conducting automatic occlusivity testing, performing automatic priming, automatic recirculating and debubbling, conducting automatic pressure tests, or performing automatic system emptying.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A method of configuring an integrated perfusion system including a heart lung machine having an RF sensor and a disposable component having an RFID tag, the method comprising steps of:
providing the RFID tag with information describing volumetric characteristics of the disposable component including sizing information;
attaching the disposable component having the RFID tag to the heart lung machine;
reading the RFID tag with the RF sensor to retrieve the volumetric characteristics of the disposable component; and
configuring operation of the heart lung machine based at least in part upon the volumetric characteristics of the disposable component retrieved by the RF sensor from the RFID tag to determine a working blood volume for the heart lung machine based on the sizing information.

2. The method of claim 1, wherein reading the RFID tag with the RF sensor comprises scanning a passive RFID tag with an RF reader.

3. The method of claim 1, wherein configuring operation of the heart lung machine comprises providing a controller, via the RF sensor, with the volumetric characteristics of the disposable component retrieved from the RFID tag by the RF sensor.

4. The method of claim 1, further comprising displaying information provided from the RFID tag to the RF sensor.

5. The method of claim 1, wherein attaching the disposable component having an RFID tag to the heart lung machine precedes reading the RFID tag with the RF sensor.

6. The method of claim 1, wherein providing the RFID tag with information describing volumetric characteristics of the disposable component includes providing the RFID tag with a minimum working volume of the disposable component.

7. The method of claim 1, wherein providing the RFID tag with information describing volumetric characteristics of the disposable component includes providing the RFID tag with a maximum working volume of the disposable component.

8. The method of claim 1, wherein providing the RFID tag with information describing volumetric characteristics of the disposable component includes providing the RFID tag with a priming volume of the disposable component.

9. A heart lung machine pack comprising:
a plurality of disposable elements including:
a tubing set having a first RFID tag secured to the tubing set, the tubing set configured for one-time use with a heart lung machine; and
a component having a second RFID tag secured to the component, the component configured for one-time use with the heart lung machine,
wherein at least one disposable element of the plurality of disposable elements has a corresponding RFID tag that contains volumetric characteristics of the at least one disposable element including sizing information to be used to determine a working blood volume for the heart lung machine; and
a housing that holds the plurality of disposable elements, wherein the housing is configured to be sealed to keep the plurality of disposable elements clean and sterile.

10. The heart lung machine pack of claim 9, wherein the component having the second RFID tag secured thereto includes one or more of a venous blood reservoir, a suction blood reservoir, a vent blood reservoir, a combined blood reservoir, an oxygenator, a heat exchanger or an arterial filter.

11. The heart lung machine pack of claim 9, wherein the first RFID tag and the second RFID tag each comprise a passive RFID tag.

12. The heart lung machine pack of claim 9, wherein the housing includes a third RFID tag that includes readable information identifying the contents of the heart lung machine pack.

* * * * *